United States Patent
Grund et al.

[11] Patent Number: 6,086,637
[45] Date of Patent: *Jul. 11, 2000

[54] TRIFLUORMETHYLPYRIDONE BASED INDOLENINE METHINE DYES

[75] Inventors: Clemens Grund, Mannheim; Helmut Reichelt, Neustadt; Andreas Johann Schmidt, Freinsheim; Frank Würthner, Ulm; Rüdiger Sens, Mannheim; Stefan Beckmann, Bad Dürkheim, all of Germany

[73] Assignee: BASF Aktiengesellschaft, Ludwigshafen, Germany

[*] Notice: This patent is subject to a terminal disclaimer.

[21] Appl. No.: 09/308,220

[22] PCT Filed: Nov. 11, 1997

[86] PCT No.: PCT/EP97/06291

§ 371 Date: May 19, 1999

§ 102(e) Date: May 19, 1999

[87] PCT Pub. No.: WO98/23688

PCT Pub. Date: Jun. 4, 1998

[30] Foreign Application Priority Data

Nov. 23, 1996 [DE] Germany .............................. 196 48 564
Dec. 7, 1996 [DE] Germany .............................. 196 50 958

[51] Int. Cl.[7] .............................. D06P 3/54; C09B 23/10; B41M 5/38
[52] U.S. Cl. .............................. 8/471; 8/922; 546/277.4; 548/469
[58] Field of Search .................... 8/471, 922; 546/277.4; 548/469, 468

[56] References Cited

U.S. PATENT DOCUMENTS 5,132,438  7/1992  Bach et al. .
5,214,140  5/1993  Bach et al. .
5,892,046  4/1999  Grund et al. .
5,962,691  10/1999  Schmidt et al. .

FOREIGN PATENT DOCUMENTS 0 399 473 A1  11/1990  European Pat. Off. .
4440066  5/1996  Germany .
5-339237  12/1993  Japan .
WO 96/15195  5/1996  WIPO .

*Primary Examiner*—Margaret Einsmann
*Attorney, Agent, or Firm*—Oblon, Spivak, McClelland, Maier & Neustadt, P.C.

[57] ABSTRACT

Indoleninemethine dyes of the formula

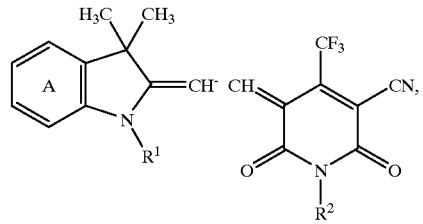

where the ring A is substituted or unsubstituted, $R^1$ is hydrogen, substituted or unsubstituted $C_1$–$C_{13}$-alkyl, $C_3$–$C_4$-alkenyl, $C_5$–$C_7$-cycloalkyl or substituted or unsubstituted phenyl, and $R^2$ is substituted or unsubstituted $C_1$–$C_{13}$-alkyl, $C_3$–$C_4$-alkenyl, substituted or unsubstituted phenyl or substituted or unsubstituted amino, are useful for dyeing or printing synthetic materials and can be thermally transferred.

4 Claims, No Drawings

TRIFLUORMETHYLPYRIDONE BASED INDOLENINE METHINE DYES

DESCRIPTION

The present invention relates to novel pyridone dyes of the formula I

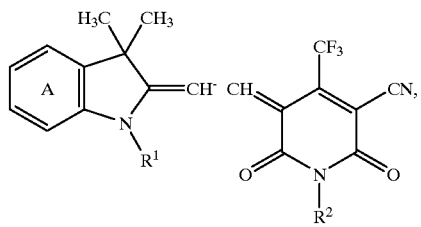

where the ring A is substituted or unsubstituted,

R$^1$ is hydrogen, C$_f$–C$_{13}$-alkyl with or without substitution and with or without interruption by from 1 to 4 oxygen atoms in ether function, C$_3$–C$_4$-alkenyl, C$_5$–C$_7$-cycloalkyl or substituted or unsubstituted phenyl, and R$^2$ is C$_1$–C$_{13}$-alkyl with or without substitution and with or without interruption by from 1 to 4 oxygen atoms in ether function, C$_3$–C$_4$-alkenyl, substituted or unsubstituted phenyl or a radical of the formula NE$^1$E$^2$, where E$^1$ and E$^2$ are identical or different and each is independently of the other hydrogen, C$_1$–C$_{13}$-alkyl with or without substitution and with or without interruption by from 1 to 3 oxygen atoms in ether function, C$_5$–C$_7$-cycloalkyl, substituted or unsubstituted phenyl, substituted or unsubstituted pyridyl, substituted or unsubstituted C$_1$–C$_{13}$-alkanoyl, C$_1$–C$_{13}$-alkoxycarbonyl, substituted or unsubstituted C$_1$–C$_{13}$-alkylsulfonyl, C$_5$–C$_7$-cycloalkylsulfonyl, substituted or unsubstituted phenylsulfonyl, substituted or unsubstituted pyridylsulfonyl, substituted or unsubstituted benzoyl, pyridylcarbonyl or thienylcarbonyl, or E$^1$ and E$^2$ join with the linking nitrogen atom to form unsubstituted or C$_1$–C$_4$-alkyl-substituted succinimido, unsubstituted or C$_f$–C$_4$-alkyl-substituted phthalimido or a 5- or 6-membered saturated heterocyclic radical with or without further hetero atoms, to a process for dyeing or printing synthetic materials using the novel dyes and to a process for their thermal transfer.

JP-A-339 237/1993 describes the preparation of 1-alkyl-3-cyano-4-trifluoromethyl-6-hydroxypyrid-2-ones. Furthermore, WO-A-96/15 195 discloses methine and azamethine dyes based on trifluoromethylpyridones.

It is an object of the present invention to provide novel indoleninemethine dyes having advantageous application properties for textile application.

We have found that this object is achieved by the indoleninemethine dyes of the formula I defined at the outset.

Any alkyl or alkenyl appearing in the abovementioned formulae may be straight-chain or branched.

Substituted alkyl appearing in the abovementioned formulae may have substituents for example, unless otherwise stated, cyclohexyl, substituted or unsubstituted phenyl, C$_1$–C$_8$-alkanoyloxy, C$_1$–C$_8$-alkylaminocarbonyloxy, C$_1$–C$_8$-alkoxycarbonyl, C$_1$–C$_8$-alkoxycarbonyloxy, the alkyl chain in the last three radicals being optionally interrupted by from 1 to 3 oxygen atoms in ether function and optionally phenyl- or phenoxy-substituted, cyclohexyloxy, phenoxy, halogen, hydroxyl, cyano, pyrazoyl or C$_1$–C$_4$-dialkylamino. Substituted alkyl generally has 1 or 2 substituents.

Alkyl in the abovementioned formulae which is interrupted by oxygen atoms in ether function is preferably alkyl interrupted by 1 or 2 oxygen atoms in ether function.

Substituted phenyl or pyridyl in the abovementioned formulae may have substituents for example, as in ring A, C$_1$–C$_8$-alkyl, C$_1$–C$_8$-alkoxy, halogen, especially chlorine or bromine, nitro, cyano or C$_1$–C$_4$-alkoxycarbonyl. Substituted phenyl or pyridyl generally has from 1 to 3 substituents.

Suitable R$^1$, R$^2$, E$^1$ and E$^2$ are each for example methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, isotridecyl [The designations isooctyl, isononyl, isodecyl and isotridecyl are trivial names derived from the alcohols obtained by the oxo process (cf. Ullmann's Encyclopedia of Industrial Chemistry, 5th Edition, Vol. A1, pages 290 to 293, and also Vol. A 10, pages 284 and 285).], 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,9-trioxadecyl, 3,6,9-trioxaundecyl, 3,6,9,12-tetraoxatridecyl, 3,6,9,12-tetraoxatetradecyl, phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2,4-dimethylphenyl, 2-, 3- or 4-methoxyphenyl, 2-, 3- or 4-ethoxyphenyl, 2-, 3- or 4-isobutoxyphenyl, 2,4-dimethoxyphenyl, 2-, 3- or 4-chlorophenyl, 2,6-dichlorophenyl, 2-, 3- or 4-nitrophenyl 2-, 3- or 4-carboxyphenyl, 2-, 3- or 4-cyanophenyl, 2-, 3- or 4-methoxy- or ethoxycarbonylphenyl, benzyl, 2-methylbenzyl, 1- or 2-phenylethyl, 2-hydroxyethyl, 2- or 3-hydroxypropyl, 2-cyanoethyl, 2- or 3-cyanopropyl, 2-acetyloxyethyl, 2- or 3-acetyloxypropyl, 2-isobutyryloxyethyl, 2- or 3-isobutyryloxypropyl, 2-methoxycarbonylethyl, 2- or 3-methoxycarbonylpropyl, 2-ethoxycarbonylethyl, 2- or 3-ethoxycarbonylpropyl, 2-methoxycarbonyloxyethyl, 2- or 3-methoxycarbonyloxypropyl, 2-ethoxycarbonyloxyethyl, 2- or 3-ethoxycarbonyloxypropyl, 2-butoxycarbonyloxyethyl, 2- or 3-butoxycarbonyloxypropyl, 2-(2-phenylethoxycarbonyloxy)ethyl, 2 or 3-(2-phenylethoxycarbonyloxy)propyl, 2-(2-ethoxyethoxycarbonyloxy)ethyl or 2- or 3-(2-ethoxyethoxycarbonyloxy)propyl.

R$^1$, E$^1$ and E$^2$ may each also be for example cyclopentyl, cyclohexyl or cycloheptyl.

E$^1$ and E$^2$ may each also be for example pyridyl, 2-, 3- or 4-methylpyridyl, 2-, 3- or 4-methoxypyridyl, formyl, acetyl, propionyl, butyryl, isobutyryl, pentanoyl, hexanoyl, heptanoyl, octanoyl, 2-ethylhexanoyl, methoxycarbonyl, ethoxycarbonyl, propoxycarbonyl, isopropoxycarbonyl, butoxycarbonyl, isobutoxycarbonyl, sec-butoxycarbonyl, methylsulfonyl, ethylsulfonyl, propylsulfonyl, isopropylsulfonyl, butylsulfonyl, cyclopentylsulfonyl, cyclohexylsulfonyl, cycloheptylsulfonyl, phenylsulfonyl, tolylsulfonyl, pyridylsulfonyl, benzoyl, 2-, 3- or 4-methylbenzoyl, 2-, 3- or 4-methoxybenzoyl, thien-2-ylcarbonyl or thien-3-ylcarbonyl.

R$^1$ and R$^2$ may each also be for example allyl or methallyl.

$E^1$ and $E^2$ joined together with the linking nitrogen atom to form a 5- or 6-membered saturated heterocyclic radical with or without further hetero atoms may be for example pyrrolidinyl, piperidinyl, morpholinyl, piperazinyl or N-($C_1$–$C_4$-alkyl) piperazinyl.

Preference is given to indoleninemethine dyes of the formula I where the ring A is unsubstituted.

Preference is further given to indoleninemethine dyes of the formula I where $R^1$ is $C_1$–$C_4$-alkyl with or without phenyl substitution.

Preference is further given to indoleninemethine dyes of the formula I where $R^2$ is $C_1$–$C_9$-alkyl with or without interruption by from 1 to 3 oxygen atoms in ether function and with or without hydroxyl or phenyl substitution or phenyl.

Particular preference is given to indoleninemethine dyes of the formula I where $R^2$ is $C_1$–$C_6$-alkyl with or without interruption by 1 or 2 oxygen atoms in ether function.

Preference is further given to indoleninemethine dyes of the formula I where $R^1$ is methyl or benzyl.

The novel indoleninemethine dyes of the formula I can be prepared by methods known per se.

For example, they can be obtained by condensation of aldehydes of the formula II

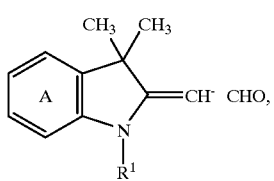

(II)

where the ring A and $R^1$ are each as defined above, with trifluoromethylpyridones of the formula III

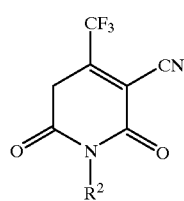

(III)

where $R^2$ is as defined above.

The intermediates for preparing the novel indoleninemethine dyes are generally compounds known per se.

It has also been found that synthetic materials can be advantageously dyed or printed by treating them with one or more of the dyes of the invention. Examples of synthetic materials are polyesters, polyamides or polycarbonates. Particularly suitable synthetic materials are materials in textile form, such as fibers, yarns, threads, knits, wovens or non-wovens composed of polyester, modified polyester, for example anionically modified polyester, blends of polyester with cellulose, cotton, viscose or wool, or polyamide. The dyeing and printing conditions are known per se and also include dyeing in supercritical carbon dioxide. The dyeings or prints obtained have high lightfastness, high brilliance and very good wetfastnesses, for example very good wash or perspiration fastness.

The present invention further provides a process for transferring dyes from a transfer to polymer-coated paper by diffusion or sublimation with the aid of an energy source, which comprises using a transfer comprising one or more indoleninemethine dyes of the formula I.

To make the transfers required for the process of the present invention, the dyes of the formula I are incorporated in a suitable organic solvent or a mixture of solvents with one or more binders with or without auxiliaries to form a printing ink. This printing ink preferably contains the dyes of the formula I in a molecularly disperse, ie. dissolved, form. The printing ink can be applied to the inert support by means of a doctor blade and air dried. Suitable organic solvents for the dyes of the formula I include for example those in which the. solubility of the dyes of the formula I at a temperature of 20° C. is greater than 1% by weight, preferably greater than 5% by weight.

Examples are ethanol, propanol, isobutanol, tetrahydrofuran, methylene chloride, methyl ethyl ketone, cyclopentanone, cyclohexanone, toluene, chlorobenzene or mixtures thereof.

Suitable binders include all resins or polymer materials which are soluble in organic solvents and which are capable of binding the dye to the inert support sufficiently firmly as to prevent rubbing off. Preference is given to those binders which, after the air drying of the printing ink, include the dye in the form of a clear, transparent film without any visible crystallization of the dye.

Such binders are mentioned for example in U.S. Pat. No. 5,132,438 or in the pertinent patent applications cited therein. Also suitable are saturated linear polyesters.

Preferred binders include ethylcellulose, ethylhydroxyethyl-cellulose, polyvinyl butyral, polyvinyl acetate, cellulose propionate or saturated linear polyesters.

The weight ratio of binder: dye generally ranges from 1:1 to 10:1.

Suitable auxiliaries include for example release agents as mentioned in U.S. Pat. No. 5,132,438 or the pertinent patent applications cited therein. Also suitable are especially organic additives which prevent the crystallizing out of the transfer dyes in the course of storage or on heating of the color ribbon, for example cholesterol or vanillin.

Suitable inert supports are described for example in U.S. Pat. No. 5,132,438 or in the pertinent patent applications cited therein. The thickness of the support generally ranges from 3 to 30 $\mu$m.

Suitable dye receiver layers include in principle all thermally stable plastics layers with affinity for the dyes to be transferred, for example modified polycarbonates or polyesters. Further details can be found for example in U.S. Pat. No. 5 132 438 or the pertinent patent applications cited therein.

The process of transfer is effected by means of an energy source, for example by means of a laser or a thermal head, for which the latter has to be heatable to a temperature of $\geq 300°$ C. so that the transfer of the dye can take place within the time range t: $0<t<15$ msec. The dye migrates out of the transfer sheet and diffuses into the surface coating of the receiving medium.

The dyes of the formula I of the present invention are notable for advantageous dye transfer application properties. They exhibit high solubility in the color ribbon (good compatibility with the binder), a high stability in the printing ink, good transferability, high image stability (ie. good lightfastness and also good stability to environmental effects, for example moisture, temperature or chemicals), and permit flexible coloristic adaptation to given subtractive primary colors as part of an optimal trichromat (highest possible brilliance of primary or secondary colors and deep neutral black).

The novel indoleninemethine dyes are also useful for printing materials by means of the inkjet process. Suitable substrates are for example paper, glass, ceramics, plastics and metals as well as those mentioned above.

The dyes of the invention can also be used for dyeing keratinous fibers, for example in hair dyeing or the dyeing of furs.

The novel dyes of the formula I are also advantageously useful for the manufacture of color filters as described for example in EP-A-399 473.

Finally, they can also be used with advantage as colorants for the manufacture of toners for electrophotography.

The Examples which follow illustrate the invention.

EXAMPLE 1 a) 100 ml of methanol and 29 g of n-hexylamine (0.287 mol) were charged initially and admixed at 30–35° C. with 32.8 g (0.287 mol) of ethyl cyanoacetate over 2 h. The mixture was subsequently stirred at 30° C. for 2 h. 25 g of piperidine were added, followed by 52.8 g (0.287 mol) of ethyl 4,4,4-trifluoroacetoacetate. The reaction mixture was then refluxed for 14 h and the solvent was removed at a temperature rising to 100° C. The rest was added while still hot to 450 g of ice and 75 ml of concentrated hydrochloric acid. The product was filtered off with suction, washed neutral with cold water and dried at 50° C. under reduced pressure, leaving 79.3 g of pyridone of formula

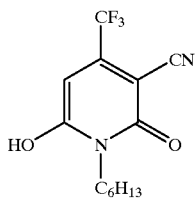

yield: 95.9% b) 4.0 g (0.02 mol) of aldehyde of the formula

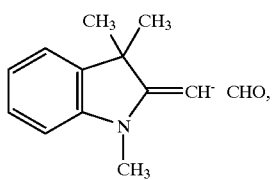

and 5.8 g (0.02 mol) of the compound described in Example 1a) were heated to 130° C. in 20 ml of acetic anhydride for 30 min. Cooling brought down a precipitate of a brilliant red dye of the formula

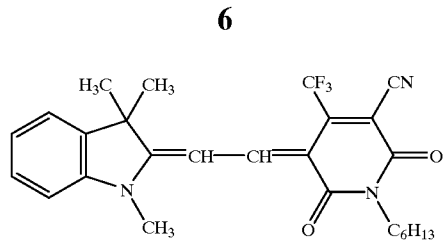

which was filtered off with suction, washed with a little methanol and dried at 50° C. under reduced pressure.

Yield: 6.6 g (70%)

$\lambda_{max}$: 538 nm ($CH_2Cl_2$)

EXAMPLE 2 a) To 210 ml of methanol and 118.3 g of 3-(2-phenoxyethoxy)propylamine (0.6 mol) were added, over 2 h, 67.9 g (0.6 mol) of ethyl cyanoacetate at from 30 to 35° C. The mixture was subsequently stirred at 30° C. for 2 h. 52.3 g of piperidine were added, followed by 110.4 g (0.6 mol) of ethyl 4,4,4-trifluoroacetoacetate. The reaction mixture was then refluxed for 14 h and the solvent was removed at a temperature rising to 100° C. The remainder was added while still hot to 1 l of ice and 157 ml of concentrated hydrochloric acid. The aqueous mixture was extracted with 500 ml of ethyl acetate, dried over sodium sulfate and subjected to reduced pressure to remove the solvent, leaving 201 g (87.5% yield) of the pyridone of the formula

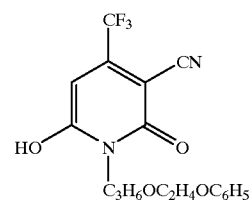

b) 4.0 g (0.02 mol) of aldehyde of the formula

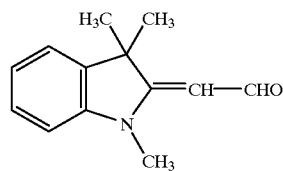

and 7.6 g (0.02 mol) of the compound described in Example 2a) were heated to 130° C. in 20 ml of acetic anhydride for 30 min. After cooling, the precipitated dye of the formula

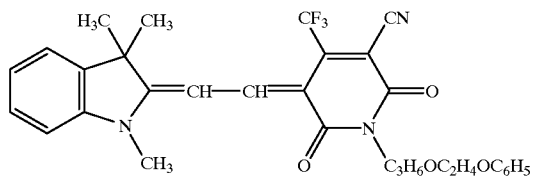

was filtered off with suction, washed a little methanol and dried at 50° C. under reduced pressure.

Yield: 6.25 g (57.8 %)

$\lambda_{max}$: 536 nm (CH$_2$Cl$_2$)

EXAMPLE 3 a) To 35.4 g (0.6 mol) of propylamine were added dropwise, at 30–35° C., 67.9 g of ethyl cyanoacetate (0.6 mol). The mixture was subsequently stirred at 30° C. for 2 h. Then 52.5 g of piperidine (0.61 mol) and 111.6 g (0.6 mol) of ethyl 4,4,4-trifluoroacetoacetate were added dropwise. The temperature rose to 53° C. The mixture was then refluxed for 10 h. The solvent was distilled off after the reaction had ended, and the remaining residue was poured hot into a mixture of 1 l of ice-water and 160 ml of concentrated hydrochloric acid. The product crystallized out at 5° C. in the course of 1 h, was filtered off with suction and washed neutral with a little water and dried at 50° C. under reduced pressure, leaving 205 g of the pyridone of the formula

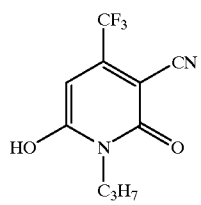

b) 4.0 g of aldehyde (0.02 mol)

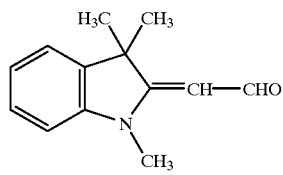

and 4.92 g (0.02 mol) of the pyridone described in Example 3a were heated to 130° C. in 20 ml of acetic anhydride for 30 min. Cooling brought down a precipitate of a red dye of the formula

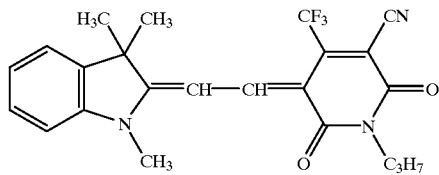

which was filtered off with suction, washed with methanol and dried at 50° C. under reduced pressure.

Yield: 6.5 g (76%)

$\lambda_{max}$: 536 nm (CH$_2$Cl$_2$)

The same method is used to obtain the dyes of the formula

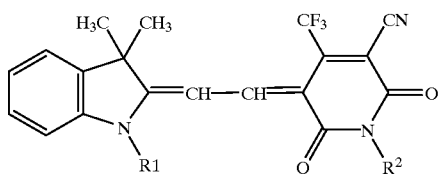

recited in Table 1 below:

TABLE 1

| Ex. No. | $R^1$ | $R^2$ | $\lambda_{max}$ [nm] (in CH$_2$Cl$_2$) |
|---|---|---|---|
| 4 | CH$_3$ | C$_2$H$_4$C$_6$H$_5$ | 536 |
| 5 | CH$_3$ | CH$_2$C$_6$H$_5$ | 536 |
| 6 | CH$_3$ | CH$_3$ | 536 |
| 7 | CH$_3$ | C$_4$H$_9$ | 536 |
| 8 | CH$_3$ | C$_2$H$_5$ | 536 |
| 9 | CH$_3$ | (CH$_2$)$_3$OCH$_3$ | 536 |
| 10 | CH$_3$ | (CH$_2$)$_2$OC$_2$H$_5$ | 536 |
| 11 | CH$_3$ | (CH$_2$)$_3$O(CH$_2$)$_2$OCH$_3$ | 536 |
| 12 | CH$_3$ | (CH$_2$)$_2$-pyrazolyl | 536 |
| 13 | CH$_3$ | (CH$_2$)$_3$—N(CH$_3$)$_2$ | 536 |
| 14 | CH$_3$ | C$_5$H$_{11}$ | 537 |
| 15 | CH$_3$ | CH$_2$CH(C$_2$H$_5$)C$_4$H$_9$ | 536 |
| 16 | CH$_3$ | C$_6$H$_5$ | 538 |
| 17 | CH$_3$ | (CH$_2$)$_2$OH | 536 |
| 18 | CH$_3$ | (CH$_2$)$_2$OCOCH$_3$ | 536 |
| 19 | C$_6$H$_5$ | C$_6$H$_{13}$ | 537 |
| 20 | CH$_2$C$_6$H$_5$ | C$_6$H$_{13}$ | 536 |
| 21 | CH$_2$C$_6$H$_5$ | C$_4$H$_9$ | 536 |
| 22 | (CH$_2$)$_2$C$_6$H$_5$ | C$_6$H$_{13}$ | 542 |
| 23 | (CH$_2$)$_2$C$_6$H$_5$ | C$_3$H$_6$OC$_2$H$_4$OC$_6$H$_5$ | 542 |
| 24 | (CH$_2$)$_2$C$_6$H$_5$ | C$_3$H$_7$ | 542 |
| 25 | (CH$_2$)$_2$C$_6$H$_5$ | C$_3$H$_6$OCH$_2$CH(C$_2$H$_5$)C$_4$H$_9$ | 542 |
| 26 | (CH$_2$)$_2$C$_6$H$_5$ | C$_2$H$_4$OC$_2$H$_5$ | 542 |
| 27 | CH$_3$ | C$_3$H$_6$OC$_2$H$_4$OC$_2$H$_5$ | 540 |
| 28 | CH$_3$ | C$_3$H$_6$OCH$_2$CH(C$_2$H$_5$)C$_4$H$_9$ | 540 |
| 29 | C$_4$H$_9$ | C$_4$H$_9$ | 538 |
| 30 | C$_4$H$_9$ | C$_3$H$_6$OCH$_2$CH(C$_2$H$_5$)C$_4$H$_9$ | 540 |
| 31 | C$_6$H$_{13}$ | (CH$_2$)$_2$C$_6$H$_5$ | 540 |
| 32 | CH$_3$ | C$_3$H$_6$OCH$_2$C$_6$H$_5$ | 538 |
| 33 | CH$_3$ | C$_2$H$_4$OC$_6$H$_4$-p-OCH$_3$ | 538 |
| 34 | CH$_3$ | CH(CH$_3$)C$_3$H$_6$CH(CH$_3$)CH$_3$ | 538 |
| 35 | CH$_3$ | C$_3$H$_6$OC$_3$H$_7$ | 538 |

Use in dyeing 10 g of a woven polyester fabric are introduced at 50° C. into 200 ml of a dyeing liquor which contains X% by weight, based on the polyester fabric, of dye and whose pH has been set at 4.5 by means of acetic acid. The fabric was treated at 50° C. for 5 min, the temperature of the liquor was then raised to 130° C. over 30 min, maintained for 60 min at that level and then cooled back down to 60° C. over 20 min.

The dyed polyester fabric was then reduction cleared by treating it at 65° C. in 200 ml of a liquor containing 5 ml/l of 32% strength by weight aqueous sodium hydroxide solution, 3 g/l of sodium dithionite and 1 g/l of an addition-product of 48 mol of ethylene oxide with 1 mol of castor oil for 15 min. The fabric was finally rinsed, neutralized with dilute acetic acid, rinsed once more and dried.

Dyes No. 1 to 35 were each employed in an amount (X) of 0.3% by weight. The dyeings obtained were a very brilliant red color and had excellent lightfastness.

Application in thermal transfer:

a) 10 g of dye are stirred, if necessary with brief heating to 80–90° C., into 100 g of a 10% strength by weight solution of a polyvinyl butyral binder in 4.5:2:2 v/v/v methyl ethyl ketone/toluene/cyclohexanone.

The mixture is applied with a 10 μm doctor blade to a 6 μm thick polyester film which has a suitable slipping layer on the back and is blown dry with a hair dryer in the course of 1 minute. Before the color ribbon can be printed, it has to be air dried for at least a further 24 hours, since residual solvents can impair the printing process.

b) The color ribbons are printed on an experimental computer-controlled apparatus equipped with a commercial thermal printing head onto commercial Color Videoprint Paper (from Hitachi).

The voltage is altered to control the energy emitted by the thermal printing head, the length of a pulse having been set to 7 ms and only one pulse being emitted at a time. The emitted energy level ranges from 0.5 to 2.0 mJ/dot.

Since the depth of the color is directly proportional to the supplied energy, it is possible to produce a color wedge for spectroscopic evaluation.

The depth of the color is plotted against the supplied energy per heating element to determine the Q* value (=energy in mJ for the absorbance value of 1) and the gradient m in 1/mJ.

The results obtained are listed in Table 2 below.

TABLE 2

| Dye No. | $Q^* [\frac{mJ}{dot}]$ | $m[\frac{1}{mJ}]$ |
|---|---|---|
| 1 | 0.93 | 2.89 |
| 2 | 0.94 | 2.54 |
| 4 | 0.98 | 2.65 |
| 5 | 1.00 | 2.25 |
| 7 | 0.93 | 2.85 |
| 11 | 0.91 | 2.84 |
| 15 | 0.98 | 2.67 |

We claim:

1. Indoleninemethine dyes of the formula I

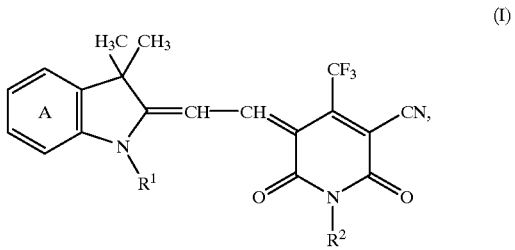

where the ring A is substituted or unsubstituted, $R^1$ is $C_1$–$C_4$-alkyl with or without substitution by phenyl, and $R^2$ is $C_1$–$C_9$-alkyl with or without interruption by from 1 to 3 oxygen atoms in either function and with or without hydroxyl or phenyl substitution or phenyl.

2. Indoleninemethine dyes as claimed in claim 1, wherein the ring A is unsubstituted.

3. A process for transferring dyes from a transfer to polymer-coated paper by diffusion or sublimation with the aid of an energy source, which comprises using a transfer comprising one or more indoleninemethine dyes of the formula I as set forth in claim 1.

4. A process for dyeing or printing synthetic materials, which comprises treating the synthetic materials with one or more indoleninemethine dyes as claimed in claim 1.

* * * * *